United States Patent
Omoto

(10) Patent No.: US 8,939,898 B2
(45) Date of Patent: Jan. 27, 2015

(54) ROTARY SELF-ADVANCING ENDOSCOPE SYSTEM, PROGRAM, AND METHOD FOR DRIVING ROTARY SELF-ADVANCING ENDOSCOPE SYSTEM

(75) Inventor: Keijiro Omoto, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 1615 days.

(21) Appl. No.: 12/168,360

(22) Filed: Jul. 7, 2008

(65) Prior Publication Data
US 2008/0262305 A1    Oct. 23, 2008

Related U.S. Application Data

(63) Continuation of application No. PCT/JP2006/325951, filed on Dec. 26, 2006.

(30) Foreign Application Priority Data

Jan. 13, 2006  (JP) .................................. 2006-006790
Jan. 13, 2006  (JP) .................................. 2006-006791

(51) Int. Cl.
*A61B 1/00*    (2006.01)
*A61B 1/005*   (2006.01)

(52) U.S. Cl.
CPC ........... *A61B 1/0016* (2013.01); *A61B 1/00154* (2013.01); *A61B 1/0051* (2013.01)
USPC ............ 600/137; 600/114; 600/117; 600/118

(58) Field of Classification Search
USPC .................................................. 600/114, 137
See application file for complete search history.

(56) References Cited

U.S. PATENT DOCUMENTS

| | | | |
|---|---|---|---|
| 5,243,967 A * | 9/1993 | Hibino .......................... | 600/109 |
| 6,726,675 B1 * | 4/2004 | Beyar ............................ | 600/137 |
| 2004/0127769 A1 * | 7/2004 | Hale et al. ..................... | 600/173 |
| 2004/0193015 A1 * | 9/2004 | Ikeda et al. ................... | 600/146 |
| 2005/0085772 A1 * | 4/2005 | Zafirelis et al. ............... | 604/131 |
| 2005/0272976 A1 * | 12/2005 | Tanaka et al. ................. | 600/114 |
| 2009/0012359 A1 * | 1/2009 | Tanaka et al. ................. | 600/114 |

FOREIGN PATENT DOCUMENTS

JP   55-45426   3/1980

\* cited by examiner

*Primary Examiner* — Matthew J Kasztejna
*Assistant Examiner* — Kevin G Barry, III
(74) *Attorney, Agent, or Firm* — Scully, Scott, Murphy & Presser, P.C.

(57) ABSTRACT

A rotary self-advancing endoscope system which produces propulsion by rotating, with a motor, a rotating cylindrical body provided on an outer periphery side of an insertion portion main body and causes the insertion portion main body to move forward into an examinee's body, wherein the system is configured to periodically repeating a combination of a state in which the rotating cylindrical body forward-rotates at a predetermined RPM and a state in which the rotating cylindrical body is stopped from rotating and releases accumulated elastic energy and, when a drive current to the motor has reached a predetermined threshold value, reverse-rotate the motor.

12 Claims, 8 Drawing Sheets

ROTARY SELF-ADVANCING ENDOSCOPE SYSTEM, PROGRAM, AND METHOD FOR DRIVING ROTARY SELF-ADVANCING ENDOSCOPE SYSTEM

CROSS REFERENCE TO RELATED APPLICATION

This application is a continuation application of PCT/JP2006/325951 filed on Dec. 26, 2006 and claims benefit of Japanese Applications No. 2006-006790 filed in Japan on Jan. 13, 2006, and No. 2007-006791 filed in Japan on Jan. 13, 2006, the entire contents of each of which are incorporated herein by their reference.

BACKGROUND OF THE INVENTION

1. Field of the Invention

The present invention relates to a rotary self-advancing endoscope system including a rotating cylindrical body at least a part on the outer periphery side of an insertion portion, a program and a driving method for drive-controlling the rotary self-advancing endoscope system.

2. Description of the Related Art

Endoscopes are widely used in a field of medicine or the like to observe a parts such as an interior of a lumen, which is not directly viewable. Such an endoscope generally includes an elongated insertion portion and has been inserted into an examinee's body by manual operation of a user.

In recent years, there have been studied endoscopes (self-propelled endoscopes) configured to be inserted by self-propulsion. There are various types of such endoscopes. An example is an endoscope configured to be inserted into a large intestine via anus, wherein the endoscope is a rotary self-propelled endoscope which has a cylindrical rotating body including a helical portion and rotatable about an axis provided on an outer periphery side of an insertion portion and is configured to be capable of being automatically inserted into a body cavity by rotating the rotating cylindrical body.

In such a self-propelled endoscope, as an inserted length of an insertion portion into an examinee's body increases, a contact area of the insertion portion with the examinee's body increases, i.e., a frictional resistance-induced load on a drive source for driving a rotating cylindrical body increases. The load may increase rapidly, for example, if kinetic friction changes to static friction at the time.

Under such circumstances, there is proposed a technique for performing constant-speed driving by detecting a rotating state of a drive source such as a motor for driving a rotating cylindrical body and controlling a current applied to the motor such that the motor rotates at a constant rotation speed. This makes it possible to insert an insertion portion at a constant pace regardless of inserted length and prevent an increase in time required for insertion.

The present invention has as an object to provide a rotary self-advancing endoscope capable of being stably inserted without reducing propulsion, a program, and a method for driving the rotary self-advancing endoscope system.

The present invention has as another object to provide a rotary self-advancing endoscope capable of predicting and avoiding a stop of a drive source of a rotating cylindrical body caused by an increase in load and improving working efficiency, a program, and a method for driving the rotary self-advancing endoscope system.

SUMMARY OF THE INVENTION

In order to achieve the above-described object, a rotary self-advancing endoscope system according to the present invention includes a rotating cylindrical body which is provided at least a part on an outer periphery side of an insertion portion to be rotatable about an insertion axis of the insertion portion, a drive source for rotating the rotating cylindrical body, and drive controlling means for controlling the drive source using a plurality of modes including a first mode of driving the drive source at a first RPM and a second mode of driving the drive source at a second RPM different from the first RPM.

A program according to the present invention is a program for causing a computer to drive-control a rotary self-advancing endoscope system including a rotating cylindrical body which is provided at least a part on an outer periphery side of an insertion portion to be rotatable about an insertion axis of the insertion portion and a drive source for rotating the rotating cylindrical body, the program causing the computer to execute a drive controlling step of controlling a rotation speed of the rotating cylindrical body to a non-constant rotation speed by controlling the drive source.

A program according to the present invention is a program for causing a computer to drive-control a rotary self-advancing endoscope system including a rotating cylindrical body which is provided at least a part on an outer periphery side of an insertion portion to be rotatable about an insertion axis of the insertion portion and a drive source for rotating the rotating cylindrical body, the program causing the computer to execute a rotation detecting step of detecting an RPM of the rotating cylindrical body by detecting a driving state of the drive source, a current detecting step of detecting a value of a current supplied to the drive source, and a drive controlling step of calculating a rate of change with time of the value of the current being detected in the current detecting step and, if the calculated rate of change is not less than a predetermined value, of performing control to temporarily stop the drive source for a predetermined time.

A rotary self-advancing endoscope system driving method according to the present invention is a rotary self-advancing endoscope system driving method for driving a rotary self-advancing endoscope system including a rotating cylindrical body which is provided at least a part on an outer periphery side of an insertion portion to be rotatable about an insertion axis of the insertion portion and a drive source for rotating the rotating cylindrical body, including a rotation detecting step of detecting an RPM of the rotating cylindrical body by detecting a driving state of the drive source, a current detecting step of detecting a value of a current supplied to the drive source, and a drive controlling step of calculating a rate of change with time of the value of the current being detected in the current detecting step and, if the calculated rate of change is not less than a predetermined value, performing control to temporarily stop the drive source for a predetermined time.

DETAILED DESCRIPTION OF THE PREFERRED EMBODIMENT(S)

An embodiment of the present invention will be described below with reference to the drawings.

Figure 1:
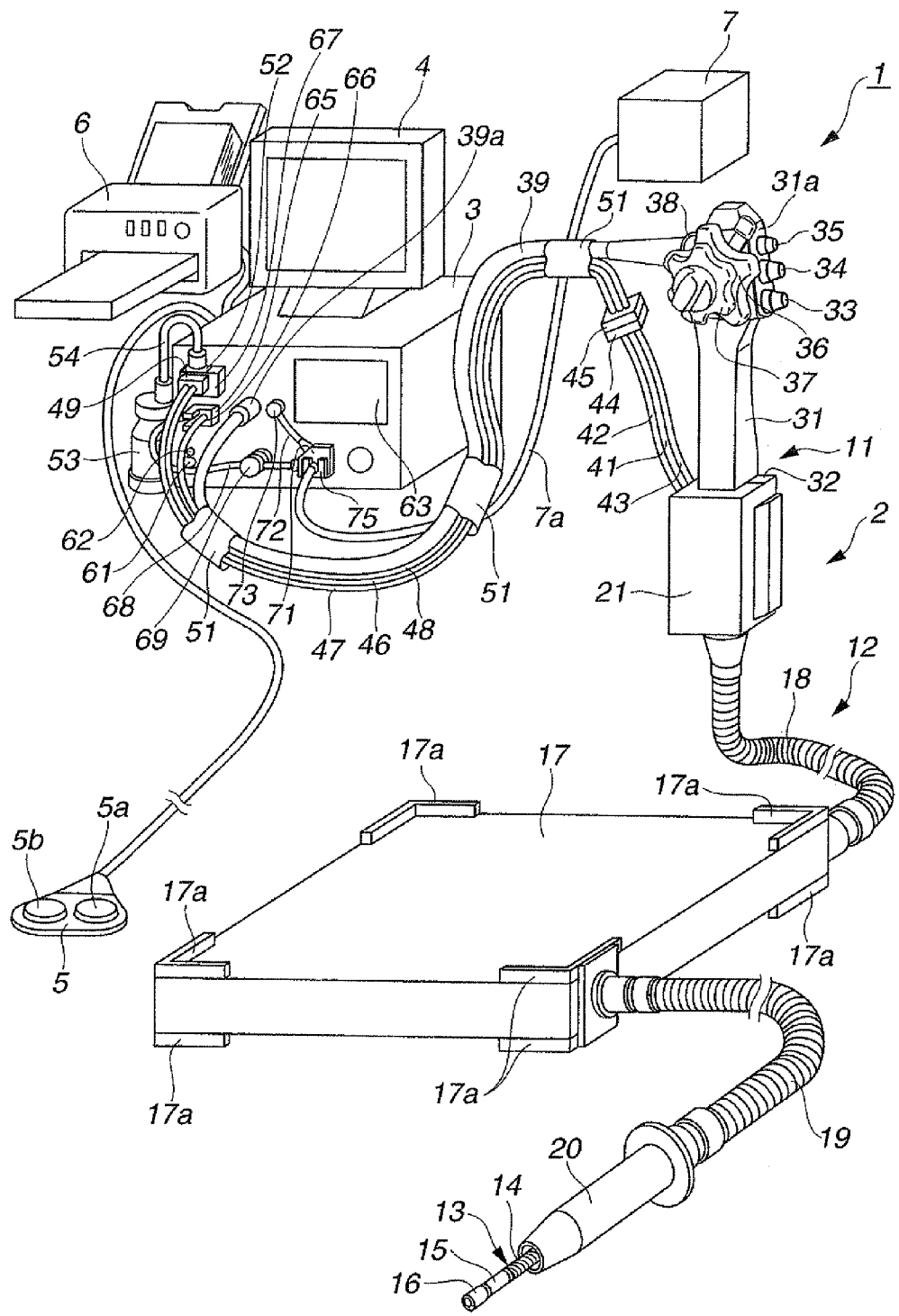
FIG. 1 is a view showing a configuration of a rotary self-advancing endoscope system according to an embodiment of the present invention.
Figure 2:
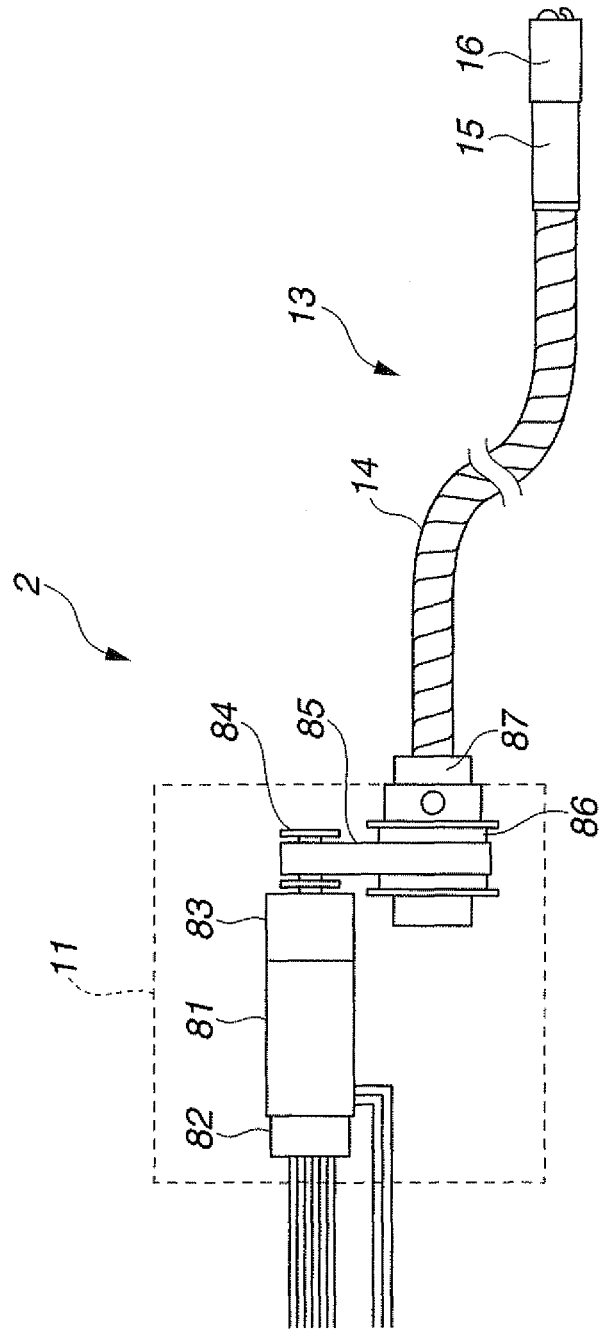
FIG. 2 is a view showing a configuration of a drive mechanism of a rotating cylindrical body in a rotary self-advancing endoscope of the embodiment.
Figure 3:
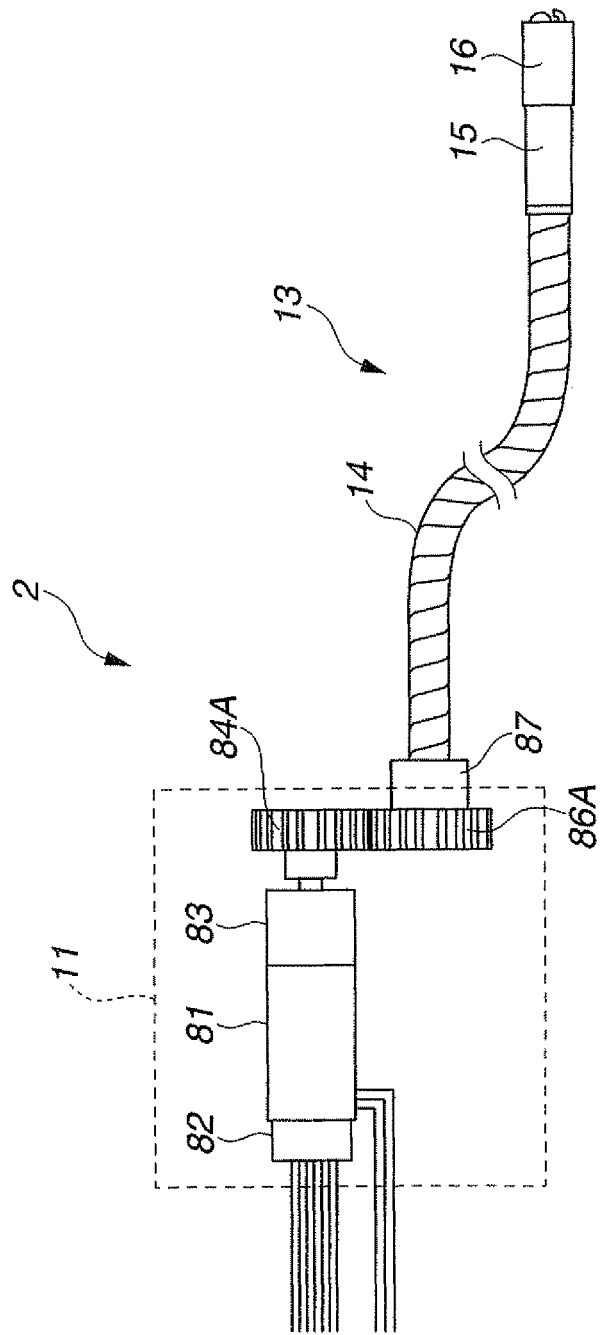
FIG. 3 is a view showing another configuration of a drive mechanism of the rotating cylindrical body in the rotary self-advancing endoscope of the embodiment.
Figure 4:
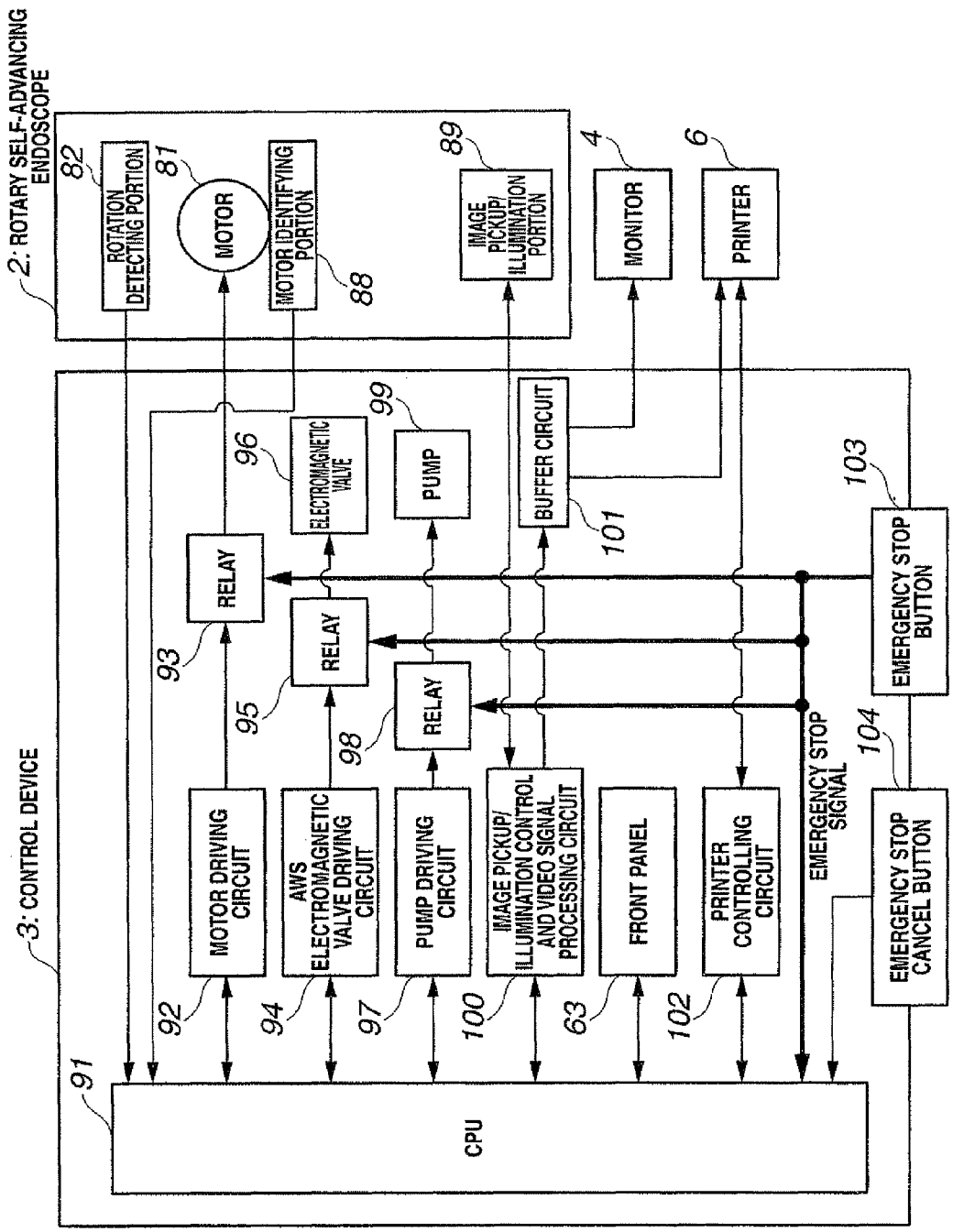
FIG. 4 is a block diagram showing an electrical configuration of the rotary self-advancing endoscope system according to the embodiment.
Figure 5:
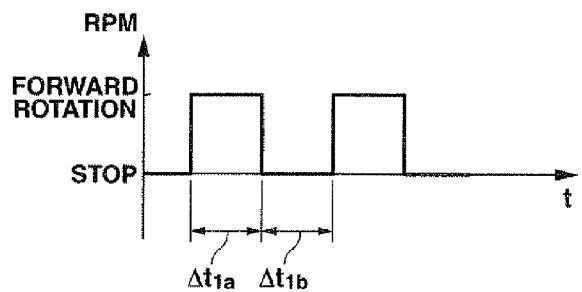
FIG. 5 is a chart showing an example of a drive pattern for driving the rotating cylindrical body in the embodiment.
Figure 6:
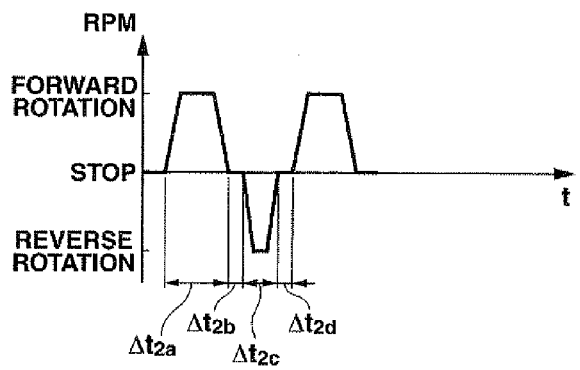
FIG. 6 is a chart showing another example of the drive pattern for driving the rotating cylindrical body in the embodiment.
Figure 7:
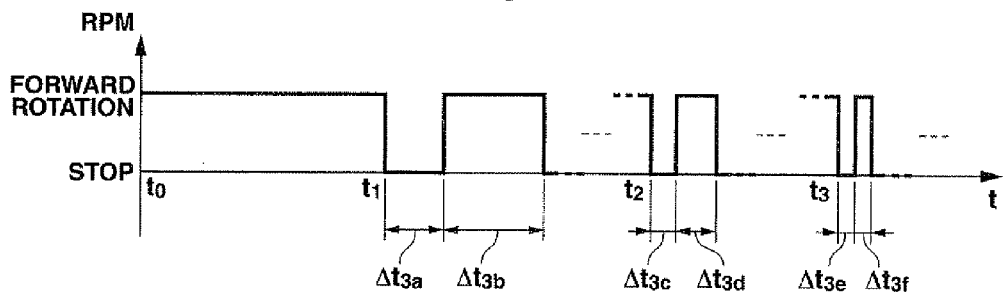
FIG. 7 is a chart showing an example in which the drive pattern for the rotating cylindrical body is changed depending on drive time in the embodiment.
Figure 8:
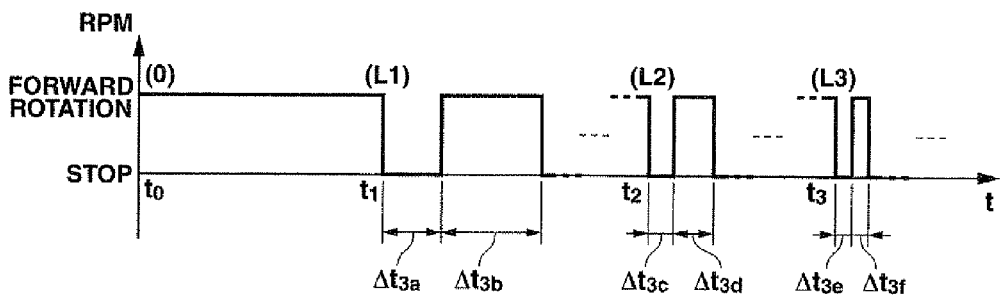
FIG. 8 is a chart showing an example in which the drive pattern for the rotating cylindrical body is changed depending on inserted length in the embodiment.
Figure 9:
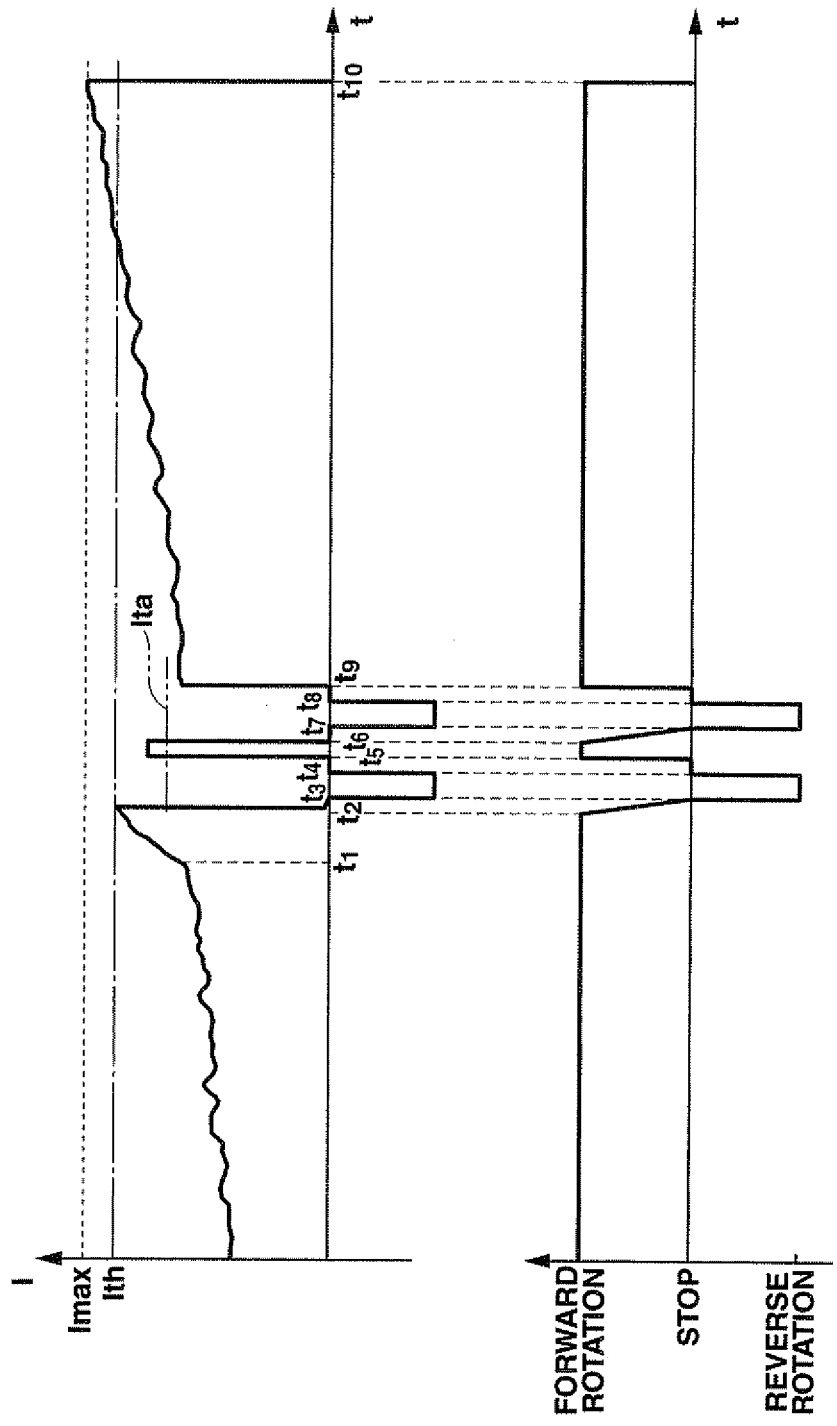
FIG. 9 is a diagram showing an example of change with time of a current value required for constant-speed driving of a motor in the embodiment.
Figure 10:
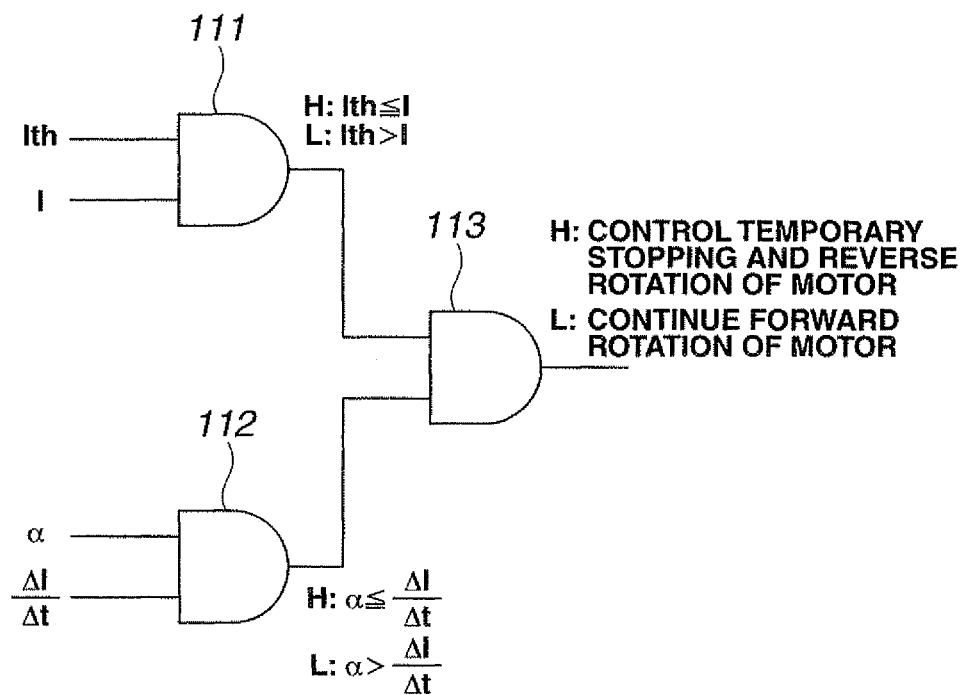
FIG. 10 is a diagram showing an example of a logic circuit for drive-controlling the motor in the embodiment.

FIGS. 1 to 11 show one embodiment of the present invention. FIG. 1 is a view showing a configuration of a rotary self-advancing endoscope system; FIG. 2, a view showing a configuration of a drive mechanism of a rotating cylindrical body in a rotary self-advancing endoscope; FIG. 3, a view showing another configuration of the drive mechanism of the rotating cylindrical body in the rotary self-advancing endoscope; FIG. 4, a block diagram showing an electrical configuration of the rotary self-advancing endoscope system; FIG. 5, a chart showing an example of a drive pattern for driving the rotating cylindrical body; FIG. 6, a chart showing another example of the drive pattern for driving the rotating cylindrical body; FIG. 7, a chart showing an example in which the drive pattern for the rotating cylindrical body is changed depending on drive time; FIG. 8, a chart showing an example in which the drive pattern for the rotating cylindrical body is changed depending on inserted length; FIG. 9, a diagram showing an example of change with time of a current value required for constant-speed driving of a motor; FIG. 10, a diagram showing an example of a logic circuit for drive-controlling the motor; and FIG. 11, a flow chart showing drive control of the motor.

The configuration of the rotary self-advancing endoscope system will be described first with reference to FIG. 1.

A rotary self-advancing endoscope system (hereinafter simply abbreviated as an endoscope system as needed) 1 includes a rotary self-advancing endoscope (hereinafter simply abbreviated as an endoscope as needed) 2, a control device 3, a monitor 4, a foot switch 5, and a printer 6.

In the endoscope 2, an elongated insertion portion 12 extends from an operation portion 11 on a near side. The insertion portion 12 includes an insertion portion main body 13 to be inserted into an examinee's body and other portions as described below for supporting the insertion portion main body 13. The insertion portion 12 is attachable/detachable to/from the operation portion 11 and is configured as, e.g., a disposable which is discarded after one-time use.

A rotating cylindrical body 14 having a helically projecting portion formed at an outer peripheral surface is provided on an outer periphery side of the insertion portion main body 13 to be rotatable about an insertion axis.

A bendable bending portion 15 is provided on a distal end side of the rotating cylindrical body 14 in the insertion portion main body 13. The bending portion 15 is configured such that a distal end of the rotating cylindrical body 14 abuts against an abutment portion on a proximal end side of the bending portion 15 to transmit propulsion caused by rotation.

A distal end rigid portion 16 is provided on a most distal end side of the insertion portion main body 13 connected to the bending portion 15. An image-pickup/illumination portion 89 (see FIG. 4) to be described later, an air supply nozzle, a water supply nozzle, a suction port, and the like are placed at the distal end rigid portion 16.

The insertion portion main body 13 described above is configured to be stored in a storage case 17 constituting a large part of the insertion portion 12 when not in use and after each use. The storage case 17 forms, e.g., a shape of a rectangular box close to a flat plate and is configured to be placeable with either principal surface up. Legs 17a for placement are provided at four corners of each principal surface. The storage case 17 is configured such that an internal height is slightly larger than a diameter of the rotating cylindrical body 14 and is smaller than twice the diameter of the rotating cylindrical body 14. With the configuration, the storage case 17 prevents the insertion portion main body 13 from twisting and wriggling due to a rotary force applied to the rotating cylindrical body 14. This is because if the insertion portion main body 13 twists and wriggles, a rotary force is expended on the twist and is not sufficiently transmitted as propulsion.

For similar reasons, the insertion portion main body 13 is configured to be prevented from twisting and wriggling and protected by an operation portion-side guide tube 18 constituting part of the insertion portion 12 between the storage case 17 and the operation portion 11 and by a distal end-side guide tube 19 constituting part of the insertion portion 12 for a part of predetermined length extending from the storage case 17 on a distal end side.

An insertion auxiliary portion 20 (which is also a part of the insertion portion 12) used when the insertion portion main body 13 is inserted into an examinee's body is provided closer to a distal end than the distal end-side guide tube 19 to loosely fit on an outer periphery of the insertion portion main body 13. The rotary self-advancing endoscope system 1 can be used, e.g., when the endoscope 2 is automatically inserted into a large intestine or the like via anus. The insertion auxiliary portion 20 is intended to allow smooth insertion while protecting an anal portion at the time of the automatic insertion.

A connector portion 21 to be connected to a motor box 32 (to be described later) of the operation portion 11 is provided on a near side of the insertion portion 12.

The operation portion 11 has a grip portion 31 with a head 31a at which various operation buttons are provided and the motor box 32 connected to the grip portion 31 on a distal end side.

The motor box 32 incorporates a motor 81 (see FIGS. 2, 3, and 4) as a drive source for driving the rotating cylindrical body 14. A bending wire (not shown) for bending the bending portion 15 described above is configured to be connected to a drive mechanism on a bending knobs side (to be described later) through connection between the motor box 32 and the connector portion 21.

Other portions, including a signal line leading to the image-pickup/illumination portion 89, are configured to be electrically connected to a signal line leading to the control device 3 side through connection between the motor box 32 and the connector portion 21.

An air-supply/water-supply button 33 for supplying air or water, a suction button 34 for suction, an image pickup button 35 for picking up a still image, a U/D bending knob 36 for bending the bending portion 15 described above in an upward (U) or downward (D) direction with respect to an observation image, an R/L bending knob 37 for bending the bending portion 15 in a right-hand (R) or left-hand (L) direction with respect to the observation image, a rotating operation lever 38 for operationally controlling forward movement/stop/backward movement of the rotating cylindrical body 14, and the like are provided at the head 31a of the grip portion 31 to be grasped by a palm.

An electric cable 39 for transmitting a signal between the image-pickup/illumination portion 89 and the control device 3 extends from the head 31a of the grip portion 31. A connector 39a provided on a distal end side of the electric cable 39 is configured to be connected to a connector receptacle of the control device 3.

An air supply tube 41, a water supply tube 42, and a suction tube 43 which are placed in the insertion portion main body 13 extend from the connector portion 21 on a near side of the insertion portion 12, and a connector 44 is provided on a proximal end side of the tubes.

The connector 44 is configured to be detachably connected to a connector 45 provided on a distal end side of an air supply relay tube 46, a water supply relay tube 47, and a suction relay tube 48. When the connector 44 is connected to the connector 45, the air supply tube 41 and air supply relay tube 46, the water supply tube 42 and water supply relay tube 47, and the suction tube 43 and suction relay tube 48 communicate with each other.

Note that the air supply tube 41, water supply tube 42, and suction tube 43 and the air supply relay tube 46, water supply relay tube 47, and suction relay tube 48 as described above constitute part of the disposable insertion portion 12.

The air supply relay tube 46, water supply relay tube 47, and suction relay tube 48 are configured to be detachably fixed to the electric cable 39 using one or more (three in the example shown in FIG. 1) temporary fasteners 51. The fixation of the air supply relay tube 46, water supply relay tube 47, and suction relay tube 48 to the electric cable 39 prevents the tubes from hanging and improves manageability of the endoscope 2.

The relay tubes 46 to 48 as described above are configured to be connected to the control device 3 on a proximal end side. The control device 3 is intended to perform control of the image-pickup/illumination portion 89, control of air supply/water supply/suction, control of the motor 81, and the like, as will be described later. The control device 3 is configured such that a water supply tank 53 used for air supply/water supply can be attached to a side surface portion.

More specifically, the suction relay tube 48 is configured to be connected to an insertion portion-side suction connecting portion 66 of the control device 3 on the proximal end side. Note that the insertion portion-side suction connecting portion 66 is detachably attached to an insertion portion-side suction connecting portion holding member 65 which is fixed to a surface of the control device 3. An air-supply and water-supply base 49 is provided on the proximal end side of the air supply relay tube 46 and water supply relay tube 47. The air-supply and water-supply base 49 is configured to be connected to an air-supply and water-supply connector connecting portion 67 which is provided on the control device 3 through an air-supply and water-supply connector 52. The air-supply and water-supply connector 52 is to be connected to the air-supply and water-supply connector connecting portion 67, is intended to connect the air-supply and water-supply base 49 described above and a water supply pipe 54 which extends from the water supply tank 53, and is configured as a single member.

The insertion portion-side suction connecting portion 66 described above is provided at one end of an insertion portion-side suction tube 68. The insertion portion-side suction tube 68 is pinched by a pinch valve 69 which is provided on a front of the control device 3 and connected to a branch portion 71. A leak-side tube 72 branches from the branch portion 71. The leak-side tube 72 is connected to a leak pipeline in the control device 3 through a connecting portion 73 which is provided at a distal end.

The insertion portion-side suction connecting portion 66, insertion portion-side suction tube 68, branch portion 71, leak-side tube 72, and connecting portion 73 described above are configured as a preassembled integral member. Of the components, the branch portion 71 is configured to be locked by a locking portion 75 which is provided at the control device 3 and be detachably fixed.

A suction device connecting base is provided at the branch portion 71 and is configured to be connected to a distal end of a suction device-side suction tube 7a which extends from a suction device 7. As the suction device 7, for example, one provided in a hospital or the like can be used. Note that the suction device 7 may, of course, be provided in the rotary self-advancing endoscope system 1 itself as part of the system configuration.

A power switch 61, an LED 62 which displays a status of power, a front panel 63 for performing various operations, and the like are provided at the control device 3. The front panel 63 includes a standby switch and a switch for controlling rotation of the rotating cylindrical body 14.

The foot switch 5 is configured to be detachably connected to the control device 3 and includes a forward switch 5a for moving the rotating cylindrical body 14 forward and a backward switch 5b for moving the rotating cylindrical body 14 backward. Note that although the foot switch 5 is used to control rotation of the rotating cylindrical body 14 in the example, the foot switch 5 may be used for other purposes.

As described above, the rotating cylindrical body 14 is configured such that a rotating state of the rotating cylindrical body 14 can be operationally controlled using any of the rotating operation lever 38 of the operation portion 11, the foot switch 5, and the control device 3.

The monitor 4 is detachably connected to the control device 3 and is configured to display a monitor image which is picked up by the image-pickup/illumination portion 89 as well as various pieces of information such as the rotating state of the rotating cylindrical body 14 and a state of torque required for rotation of the rotating cylindrical body 14.

The printer 6 is configured to be detachably connected to the control device 3 and to, when the image pickup button 35 of the endoscope 2 is pressed, print out a still image under control of the control device 3.

The configuration of a drive mechanism for the rotating cylindrical body 14 in the rotary self-advancing endoscope 2 will be described with reference to FIG. 2.

The motor box 32 of the operation portion 11 incorporates the motor 81 as the drive source. The motor 81 is configured to, e.g., be capable of forward driving and reverse driving. The number of revolutions per unit time of the motor 81 is detected by a rotation detecting portion 82 serving as rotation detecting means which is attached to the motor 81.

A rotary drive force generated by the motor 81 is reduced in speed through a reducer 83 and transmitted to a first pulley 84. A belt 85 hangs on the first pulley 84 and then on a second pulley 86. With the configuration, a drive force from the first pulley 84 is transmitted to the second pulley 86 through the belt 85.

The second pulley 86 is configured to rotate integrally with the rotating cylindrical body 14 through a rotation transmitting member 87. Accordingly, a rotary drive force transmitted to the second pulley 86 causes the rotating cylindrical body 14 to rotate about the insertion axis of the insertion portion main body 13. Note that only the rotating cylindrical body 14 rotates, and contents (the signal line leading to the image-pickup/illumination portion 89 to be described later, the air supply tube 41, the water supply tube 42, the suction tube 43, and the like) of the insertion portion main body 13 inside the rotating cylindrical body 14 are not affected by the rotation.

Note that although a drive force from the motor 81 is transmitted to the rotating cylindrical body 14 using the belt 85 and the pulleys 84 and 86 in the example shown in FIG. 2, the drive mechanism may be configured, e.g., in a manner as shown in FIG. 3.

In the example shown in FIG. 3, a rotary drive force generated by the motor 81 is reduced in speed through the reducer 83 and then transmitted to a first gear 84A. The first gear 84A meshes with a second gear 86A. The second gear 86A is configured to rotate integrally with the rotating cylindrical body 14 through the rotation transmitting member 87.

The present invention is not limited to the examples as shown in FIGS. 2 and 3, and a drive force from the motor 81 can be transmitted to the rotating cylindrical body 14 using various other drive mechanisms. Additionally, although a drive force from the motor 81 is transmitted from a near side end of the rotating cylindrical body 14 in the examples as shown in FIGS. 2 and 3, the present invention is not limited to this. A drive force may be transmitted by any one part (or all parts) of the rotating cylindrical body 14. The one part transmitting a drive force may be on a proximal end side of, on the distal end side of, or midway along the rotating cylindrical body 14.

The rotating cylindrical body 14 is a member obtained by helically winding a metal element wire such that the helically projecting portion is formed at the outer peripheral surface. More specifically, a metal element wire is an elongated flat plate made of a metal such as stainless steel. The metal element wire is formed such that a vertical section in a longitudinal direction has a general S-shape. The metal element wire whose section has the general S-shape is helically wound such that edges of adjacent loops engage with each other, thereby forming the rotating cylindrical body 14 constituting an elongated tube as an integral.

When the rotating cylindrical body 14 rotates, the helically projecting portion at the outer peripheral surface abuts against an inner wall of a cavity of an examinee's body to generate propulsion, and the rotating cylindrical body 14 itself attempts to move ahead in an insertion direction. At the time, a distal end surface of the rotating cylindrical body 14 abuts against an abutment portion on the proximal end side of the bending portion 15 to press the bending portion 15 and distal end rigid portion 16, and the insertion portion main body 13 is inserted into the examinee's body.

The bending portion 15 provided at a distal end portion of the insertion portion main body 13 is a part for freely bending the distal end rigid portion 16 in an U/D (upward/downward) direction and an R/L (right-hand/left-hand) direction to direct, in a desired direction, the distal end rigid portion 16 connected on a side closer to the distal end.

The image-pickup/illumination portion 89 (see FIG. 4) including image pickup elements (an image pickup portion) such as an image pickup optical system for picking up an image of an examinee's body and a CCD and light sources (an illumination portion) such as an illumination optical system for illuminating an examinee's body, an image of which is to be picked up, and an LED is placed in the distal end rigid portion 16. The water supply nozzle for cleaning the optical systems, the air supply nozzle for blowing off water droplets left after cleaning by the water supply nozzle, and the suction port for suction are further placed at the distal end rigid portion 16. The water supply nozzle, air supply nozzle, and suction port are connected to the water supply tube 42, air supply tube 41, and suction tube 43, respectively.

The electrical configuration of the rotary self-advancing endoscope system 1 will be described with reference to FIG. 4.

The control device 3 includes a CPU 91, a motor driving circuit 92, a relay 93, an AWS electromagnetic valve driving circuit 94, a relay 95, an electromagnetic valve 96, a pump driving circuit 97, a relay 98, a pump 99, an image-pickup/illumination control and video signal processing circuit 100, a buffer circuit 101, the front panel 63, a printer controlling circuit 102, an emergency stop button 103, and an emergency stop cancel button 104.

The endoscope 2 includes the motor 81, the rotation detecting portion 82, a motor identifying portion 88, and the image-pickup/illumination portion 89.

The CPU 91 is control means for controlling the rotary self-advancing endoscope system 1 in a centralized manner and also serves as drive controlling means for drive-controlling the motor 81 through the motor driving circuit 92.

The motor driving circuit 92 is connected to the motor 81 through the relay 93 and is drive controlling means for drive-controlling the motor 81 under control of the CPU 91, which executes a predetermined control program. The motor driving circuit 92 also serves as current detecting means for detecting a value of a current which drives the motor 81 and outputting the detected value to the CPU 91 whenever necessary. The CPU 91 is configured to, if the detected value has reached a predetermined upper limit current value Imax, perform control to automatically stop driving of the motor 81 for safety.

The rotation detecting portion 82 is intended to detect an RPM of the motor 81, and a detection result from the rotation detecting portion 82 is outputted to the CPU 91. The CPU 91 is configured to control constant-speed driving of the motor 81 and the like on the basis of the RPM detected by the rotation detecting portion 82.

The motor identifying portion 88 is intended to output motor identifying information indicating a type of the motor 81 incorporated in the endoscope 2 to the CPU 91. The endoscope 2 may incorporate different types of motors 81 as the drive source. A driving method changes according to the type of the motor 81. The CPU 91 is thus configured to acquire the type of the motor 81 incorporated in the connected endoscope 2 from the motor identifying portion 88 and control the motor driving circuit 92 to cause the motor 81 to perform driving appropriate for the type. Note that the motor identifying portion 88 may be configured to actively output a motor identifying signal when the endoscope 2 and control device 3 are connected to each other or may be nonvolatile memory or the like from which the motor identifying information is passively read by the CPU 91.

The AWS electromagnetic valve driving circuit 94 is intended to drive the electromagnetic valve 96 for controlling air supply (A), water supply (W), and suction (S) through the relay 95 under control of the CPU 91.

The pump driving circuit 97 is intended to drive the pump 99 through the relay 98 under control of the CPU 91. The pump 99 is a pump used for air supply/water supply.

The image-pickup/illumination control and video signal processing circuit 100 is connected to the image-pickup/illumination portion 89. Under control of the CPU 91, the image-pickup/illumination control and video signal processing circuit 100 supplies power for illumination to an illumination portion, supplies a drive clock and the like to an image pickup portion, and subjects a video signal outputted from the image pickup portion to various video signal processes.

The image-pickup/illumination control and video signal processing circuit 100 is also connected to the buffer circuit 101. The buffer circuit 101 is connected to the monitor 4 and to the printer 6. As described above, when the image pickup button 35 of the operation portion 11 is pressed, a still image is recorded. If display of an observation image on the monitor 4 is stopped at the time, manual operation suffers inconvenience. For this reason, the image-pickup/illumination control and video signal processing circuit 100 is connected to the monitor 4 to output video for observation and is connected to the printer 6 to output video for image recording. This makes it possible to, even when the image pickup button 35 is pressed, and a still image is printed out from the printer 6, continue to observe a moving image on the monitor 4.

The front panel 63 is operation inputting means which is constructed by arranging various switches, an LED, and the like. The front panel 63 is configured to, when a button operation or the like is performed, output an operation signal to the CPU 91. The front panel 63 includes the standby switch. When the standby switch is pressed, control signals are simultaneously sent from the CPU 91 to the motor driving circuit 92, AWS electromagnetic valve driving circuit 94, pump driving circuit 97, and image-pickup/illumination control and video signal processing circuit 100, thereby stopping the motor 81, supply of drive power to the AWS electromagnetic valve 96, the pump 99, and supply of power to the image-pickup/illumination portion 89. It is possible to replace an NS portion with another in the state. When the standby switch is pressed again after replacement of the NS portion, the stopped functions are restored to original operating states.

The printer controlling circuit 102 is intended to control operation of the printer 6 under control of the CPU 91. For example, the printer controlling circuit 102 is configured to, when the image pickup button 35 provided at the operation portion 11 of the endoscope 2 is pressed, control the printer 6 to print a still image accumulated in the buffer circuit 101.

The emergency stop button 103 is connected to the CPU 91 and relays 93, 95, and 98 and is an operation button for enabling an emergency stop mode. As described above, the CPU 91 detects a value of a drive current for the motor 81 and, if the detected value has reached the upper limit current value Imax, performs control to automatically stop driving of the motor 81. The endoscope system 1 is configured by being further provided with the emergency stop button 103 such that various operations can be urgently stopped by manual operation. More specifically, if the emergency stop button 103 is pressed, an emergency stop signal is sent, and the CPU 91 recognizes, regardless of any circumstance, that there is an emergency and stops the motor driving circuit 92, AWS electromagnetic valve driving circuit 94, and pump driving circuit 97. In the meantime, the emergency stop signal from the emergency stop button 103 is directly outputted to the relays 93, 95, and 98, thereby breaking electrical connection between the motor driving circuit 92 and the motor 81, electrical connection between the AWS electromagnetic valve driving circuit 94 and the electromagnetic valve 96, and electrical connection between the pump driving circuit 97 and the pump 99. Note that electrical connection between the image-pickup/illumination control and video signal processing circuit 100 and the image-pickup/illumination portion 89 is not broken because the electrical connection is required to safely withdraw the endoscope 2 or perform a procedure later.

The emergency stop cancel button 104 is an operation button for disabling the emergency stop mode, having been enabled by the emergency stop button 103 described above, and is configured to fulfill a function by being pressed long enough The configuration which requires the emergency stop cancel button 104 to be pressed long enough in order to disable the emergency stop mode is intended to confirm an intent of an operator that he/she has removed a cause of an emergency stop.

Some examples of a drive pattern in control of the motor 81 by the CPU 91 through the motor driving circuit 92 will be described with reference to FIGS. 5 to 8.

FIG. 5 shows, as a waveform, an example of a drive pattern for driving the rotating cylindrical body 14 with the motor 81.

The example shown in FIG. 5 illustrates a drive pattern including repetition of an operation of rotating the motor 81 in a forward rotation direction (a direction which moves the rotating cylindrical body 14 into an examinee's body) at a predetermined RPM for a fixed time $\Delta t1a$ in a first mode and then stopping the motor 81 for a fixed time $\Delta t1b$ (where $\Delta t1b$ satisfies $\Delta t1a > \Delta t1b$) in a second mode. Note that although the example is configured to satisfy $\Delta t1a > \Delta t1b$, the present invention is not limited to this, and the example may be configured to satisfy $\Delta t1a \leq \Delta t1b$.

The rotating cylindrical body 14 is constructed by, e.g., helically winding a metal element wire, as described above. When the proximal end side of the rotating cylindrical body 14 is driven by the motor 81, elastic energy is accumulated in the rotating cylindrical body 14. For this reason, the proximal end side of the rotating cylindrical body 14 rotates immediately after a start of the driving while the distal end side does not rotate immediately. After the proximal end side rotates for a certain time, the distal end side starts to rotate. Accordingly, the fixed time $\Delta t1b$, for which the motor 81 is to be stopped, is desirably set in consideration of a time constant which allows relaxation of the entire rotating cylindrical body 14. Specific examples of setting the drive time $\Delta t1a$ and the stop time $\Delta t1b$ include setting the drive time $\Delta t1a$ to 5 seconds and the stop time $\Delta t1b$ to 2 seconds. It is possible to perform air supply/water supply, still shooting, or the like during the stop time of 2 seconds.

Note that examples of the RPM at the time of forward rotation include 60 rpm, 70 rpm, 80 rpm, 90 rpm, and 100 rpm. Also note that the present system may be configured such that a desired RPM can be selected using the operation portion 11 of the endoscope 2, the front panel 63 of the control device 3, the foot switch 5, and the like.

The distal end side of the rotating cylindrical body 14 is under no constraints at the time of rotation and has a rotationally free end. The proximal end side of the rotating cylindrical body 14 may have a rotationally fixed end or may have a free end. A fixed end is achieved by fixing a rotation axis of the motor 81 during a stop while a free end is achieved by leaving the rotation axis of the motor 81 rotatable. Either end can be adopted. If the proximal end side has a fixed end, the elastic energy of the rotating cylindrical body 14 is released from only the distal end side. On the other hand, if the proximal end side is configured to have a free end, the elastic energy of the rotating cylindrical body 14 can be released from both the distal end side and proximal end side. A free end is thus more desirable for efficient release.

The driving as shown in FIG. 5 makes it possible to release accumulated elastic energy during the stop time $\Delta t1b$ and restore the rotating cylindrical body 14 to a flexible state capable of efficiently transmitting a rotary force. Additionally, the driving can reduce a load on the motor 81 and suppresses heat generated by the motor 81. The rotating cylindrical body 14 in the flexible state has an advantage of being easy to insert into an examinee's body. The provision of the stop time $\Delta t1b$ makes it possible to allow an examinee's body time to return to a natural posture. The advantages result in smooth and efficient insertion.

Another example of the drive pattern for driving the rotating cylindrical body 14 with the motor 81 will be described with reference to FIG. 6.

A drive pattern shown in FIG. 6 includes forward rotation and stop and further includes reverse rotation during the stop.

More specifically, the RPM is gradually increased after a start of forward rotation. When the RPM has reached a predetermined RPM, the RPM is kept for some time. After that, the RPM is gradually reduced, and the forward rotation is stopped. A time from when the forward rotation is started to when the forward rotation is stopped will be denoted by $\Delta t2a$.

The rotating cylindrical body 14 is then stopped for a predetermined time $\Delta t2b$.

After that, reverse rotation is started, and the RPM in a reverse rotation direction is gradually increased. When the RPM has reached a predetermined RPM, the RPM is kept for some time. After that, the RPM in the reverse rotation direction is gradually reduced, and the reverse rotation is stopped. A time from when the reverse rotation is started to when the reverse rotation is stopped will be denoted by $\Delta t2c$.

The rotating cylindrical body 14 is stopped for a predetermined time $\Delta t2d$. After that, the pattern of forward rotation, stop, reverse rotation, and stop is repeated in the manner as described above.

If the reverse rotation time is longer than the forward rotation time, the rotating cylindrical body 14 may move backward instead of moving forward. Accordingly, a drive pattern satisfying a relationship of $\Delta t2a > \Delta t2c$ is adopted here. A drive pattern satisfying a relationship of $\Delta t2c > \Delta t2b$ and a relationship of $\Delta t2c > \Delta t2d$ is desirable to minimize a time to when the distal end rigid portion 16 of the insertion portion main body 13 reaches a target part of an examinee's body.

Note that a specific example of setting the times includes setting the forward rotation time $\Delta t2a$ to 10 seconds, the stop time $\Delta t2b$ to 1 second, the reverse rotation time $\Delta t2c$ to 2 seconds, and the stop time $\Delta t2d$ to 1 second.

As described with reference to the example shown in FIG. 5, RPMs which can be set at the time of forward rotation include 60 rpm, 70 rpm, 80 rpm, 90 rpm, and 100 rpm. An RPM at the time of reverse rotation may be equal to or different from the one at the time of forward rotation.

Use of the drive pattern as shown in FIG. 6 makes it possible to obtain almost same effects as the effects obtained by use of the drive pattern as shown in FIG. 5. Since elastic energy accumulated in the rotating cylindrical body 14 is actively released by reverse rotation, it is possible to more efficiently restore original flexibility of the rotating cylindrical body 14.

An example in which the drive pattern for the rotating cylindrical body 14 is changed depending on drive time will be described with reference to FIG. 7.

In a drive pattern shown in FIG. 7, a continuous forward rotation time immediately after a start of driving is made long, and a drive cycle composed of forward rotation and stop is made to decrease with an increase in time which has elapsed since the start of the driving of the motor 81.

More specifically, after forward driving of the rotating cylindrical body 14 is started at a time t0, the rotating cylindrical body 14 is continuously driven until a time t1 is reached. A first continuous drive time (t1−t0) is set in consideration of a time required for a rotary drive force which has started to be transmitted from the proximal end side of the rotating cylindrical body 14 to reach the distal end side of the rotating cylindrical body 14.

When the time t1 is reached, the driving is stopped. The stop is continued for a time $\Delta t3a$.

Driving is started again at a time (t1+$\Delta t3a$), and the driving is performed for a time $\Delta t3b$ ($\Delta t3a < \Delta t3b$, (t1−t0) > $\Delta t3b$). Driving with a combination of the stop time $\Delta t3a$ and the drive time $\Delta t3b$ is performed until a predetermined time t2.

When the predetermined time t2 is reached, the motor 81 switches to driving with a combination of a stop time $\Delta t3c$ and a drive time $\Delta t3d$ ($\Delta t3c < \Delta t3d$). The driving is performed until a predetermined time t3. Note that the stop time $\Delta t3a$ and stop time $\Delta t3c$ satisfy a relationship of $\Delta t3a > \Delta t3c$, and the drive time $\Delta t3b$ and drive time $\Delta t3d$ satisfy a relationship of $\Delta t3b > \Delta t3d$.

After that, when the predetermined time t3 is reached, the motor 81 switches to driving with a combination of a stop time $\Delta t3e$ and a drive time $\Delta t3f$ ($\Delta t3e < \Delta t3f$). Note that the stop time $\Delta t3c$ and stop time $\Delta t3e$ satisfy a relationship of $\Delta t3c > \Delta t3e$, and the drive time $\Delta t3d$ and drive time $\Delta t3f$ satisfy a relationship of $\Delta t3d > \Delta t3f$.

A specific example of setting the times includes setting the drive time $\Delta t3b$ to 10 seconds, the drive time $\Delta t3d$ to 5 seconds, the drive time $\Delta t3f$ to 3 seconds, the stop time $\Delta t3a$ to 5 seconds, the stop time $\Delta t3c$ to 3 seconds, and the stop time $\Delta t3e$ to 1 second.

If the rotating cylindrical body 14 is reverse-driven to withdraw the endoscope 2 from an examinee's body, the rotating cylindrical body 14 may be driven with a cycle composed of the stop time $\Delta t3e$ and the drive time $\Delta t3f$ immediately after a start of the reverse rotation, driven with a cycle composed of the stop time $\Delta t3c$ and the drive time $\Delta t3d$, and then driven with a cycle composed of the stop time $\Delta t3a$ and the drive time $\Delta t3b$.

As a time which has elapsed since a start of driving increases, i.e., an inserted length of the insertion portion main body 13 into an examinee's body increases, friction between the rotating cylindrical body 14 and a body cavity of the examinee's body increases, and torque required for constant-speed rotation increases. Accordingly, elastic energy accumulated in the rotating cylindrical body 14 per unit time is likely to increase with an increase in a time which has elapsed since a start of driving. Use of the drive pattern as shown in FIG. 7 makes it possible to prevent elastic energy accumulated in the rotating cylindrical body 14 from becoming too large and allows efficient insertion.

Note that although a forward rotation time and a stop time are both made to decrease with an increase in time which has elapsed since a start of driving in the example, the present invention is not limited to this. More specifically, since elastic energy accumulated in the rotating cylindrical body 14 per unit time is likely to increase as the rotating cylindrical body 14 is inserted farther into an examinee's body, for example, elastic energy accumulated during the drive time $\Delta t3f$ and elastic energy accumulated during the drive time $\Delta t3b$ may be almost on a same level. In the case, since driving needs to be stopped for a same duration to release elastic energy, the stop times $\Delta t3a$, $\Delta t3c$, and $\Delta t3e$ may be set to have almost a same duration regardless of a time which has elapsed since a start of driving. Accordingly, a relationship of $\Delta t3a > \Delta t3c > \Delta t3e$ does not hold, and a relationship of $\Delta t3c < \Delta t3d$ and a relationship of $\Delta t3e < \Delta t3f$ do not always hold.

Although the drive cycle is changed stepwise at the time t1, time t2, time t3, and the like in the example, the drive cycle may, of course, be continuously changed. Additionally, the RPM may be changed at the time t1, time t2, time t3, and the like (the RPM may be changed stepwise or may be continuously changed).

Although a case where a drive waveform as shown in FIG. 5 is used has been illustrated with reference to FIG. 7, a drive waveform as shown in FIG. 6 can, of course, be used instead.

An example in which the drive pattern for the rotating cylindrical body 14 is changed depending on inserted length will be described with reference to FIG. 8.

While the above-described drive pattern shown in FIG. 7 is changed depending on a time which has elapsed since a start of driving of the motor 81, the drive pattern shown in FIG. 8 is changed depending on an inserted length L into an examinee's body. An appearance of the pattern is similar to an appearance of the pattern shown in FIG. 7.

More specifically, the rotating cylindrical body 14 is continuously driven until the inserted length reaches L1.

When the inserted length has reached L1, driving with a combination of the stop time Δt3a and the drive time Δt3b (the drive time Δt3b corresponds to a predetermined first inserted length) is performed. The driving is performed until the inserted length reaches L2.

When the inserted length has reached L2, driving with a combination of the stop time Δt3c and the drive time Δt3d (the drive time Δt3d corresponds to a predetermined second inserted length smaller than the above-described first inserted length) is performed. The driving is performed until the inserted length reaches L3.

After that, when the inserted length has reached L3, driving with a combination of the stop time Δt3e and the drive time Δt3f (the drive time Δt3f corresponds to a predetermined third inserted length smaller than the above-described second inserted length) is performed.

Torque required to drive the rotating cylindrical body 14 is likely to depend more precisely on inserted length than on drive time. Use of the drive pattern as shown in FIG. 8 makes it possible to more reliably control elastic energy accumulated in the rotating cylindrical body 14.

Note that although the drive cycle is changed depending on the inserted length L in the example shown in FIG. 8, the present invention is not limited to this, and the RPM may be changed depending on the inserted length L. As described above, the RPM may sometimes be changed depending on time (FIG. 7) or inserted length (FIG. 8) in order to improve insertability.

Detection of the inserted length with a separately provided sensor makes it possible to automatically perform control as described above.

Variations as described with reference to FIG. 7 can be similarly applied to FIG. 8.

Control of the motor 81 based on the drive patterns as described above is performed by the CPU 91 controlling the motor driving circuit 92 in accordance with a predetermined program.

Although a rectangular waveform and a trapezoidal waveform have been taken as examples in the above description, the present invention is not limited to these. An appropriate drive pattern with a triangular waveform, sine curve, or the like can be used instead.

A drive pattern including forward rotation and stop or forward rotation, stop, and reverse rotation has been described above. However, in a broader sense, the drive pattern may be any drive pattern that controls an RPM of the rotating cylindrical body 14 to be variable. More specifically, even if the rotating cylindrical body 14 is not completely stopped, a certain degree of effect can be obtained only by fluctuating the RPM. The RPM may be changed continuously or stepwise.

Switches for changing operation modes such as a drive cycle, a ratio between a forward rotation time and a stop time, a ratio among a forward rotation time, a stop time, and a reverse rotation time, and a drive waveform may be provided at the operation portion 11, the front panel 63 of the control device 3, or the like.

Automatic control, such as a process of detecting torque for rotating the rotating cylindrical body 14 on the basis of, e.g., a drive current for the motor 81, decreasing duration of the drive cycle if the torque is high, and increasing the duration of the drive cycle if the torque is low, may be performed.

In the above description, a drive pattern including forward rotation and stop or forward rotation, stop, and reverse rotation is achieved by automatic control of the control device 3. Alternatively, an operator may manually achieve the drive pattern by operating the rotating operation lever 38 of the operation portion 11 or the foot switch 5. In the case, the present invention is not limited to a configuration in which the rotating cylindrical body 14 is driven by the motor 81, and a configuration in which the rotating cylindrical body 14 is driven by being manually rotated using, e.g., a rotating handle may be adopted instead. It will, of course, be appreciated that the automatic control reduces a load on an operator.

Control over time of the motor 81 by the CPU 91 through the motor driving circuit 92 will be described with reference to FIGS. 9 to 11. Note that although a case where the motor 81 is driven at a constant speed will be illustrated for the sake of simplicity in the description with reference to FIGS. 9 to 11, a following description can also be applied to a case where the motor 81 is driven using the above-described patterns as shown in FIGS. 5 to 8.

An example of a change with time of a value of a current required to drive the motor 81 at a constant speed will be described first with reference to FIG. 9.

The CPU 91 controls a current supplied to the motor 81 through the motor driving circuit 92 on the basis of an RPM detected by the rotation detecting portion 82 such that the motor 81 is driven at a constant speed (the first mode). A value of a current supplied to the motor 81 is considered to be almost proportional to torque produced by the motor 81.

At the time, as the inserted length of the insertion portion main body 13 into an examinee's body increases, friction between the rotating cylindrical body 14 and a body cavity of the examinee's body increases, and torque required for constant-speed rotation increases. An overall increase in current value in FIG. 9 indicates this.

The CPU 91 sets the predetermined upper limit current value Imax to stop driving of the motor 81 if a current supplied to the motor 81 has reached the predetermined upper limit current value Imax.

Note that in actual practice, the control using the upper limit current value Imax alone may cause inconvenience. More specifically, the rotating cylindrical body 14 and a body cavity of an examinee's body are in a kinetic friction state at the time of normal driving. However, the rotating cylindrical body 14 and body cavity may fall into a static friction state before the rotating cylindrical body 14 reaches a target part, for some reasons. In such a case, the torque increases rapidly, and when a current supplied to the motor 81 has reached the upper limit current value Imax, driving of the motor 81 is stopped. A predetermined series of operations for resuming driving of the motor 81 and the like needs to be performed at the time.

Under the circumstances, the CPU 91 is configured to predict whether a current value reaches the upper limit current value Imax while monitoring the current value for a rapid increase and the like and, if the current value is predicted to reach the upper limit current value Imax, perform a predetermined process for reducing the torque (the second mode) before the current value reaches the upper limit current value Imax.

More specifically, the CPU 91 sets a threshold value Ith obtained by multiplying the upper limit current value Imax by a predetermined coefficient of less than 1. A specific example of the threshold value Ith includes a value obtained by multiplying the upper limit current value Imax by 0.9. The CPU 91 performs monitoring to check whether a current value I being detected has reached the threshold value Ith.

The CPU 91 calculates a variation $\Delta I$ in the current value I being detected per a predetermined time $\Delta t$, i.e., a rate of change with time of the current value I, $\Delta I/\Delta t$, and performs monitoring to check whether the rate of change $\Delta I/\Delta t$ has become not less than a predetermined value $\alpha$. Note that $\Delta t$ used when calculating the rate of change of the current value I, $\Delta I/\Delta t$, desirably has a certain degree of duration to avoid influences of tiny noise and the like.

The CPU 91 is configured to temporarily stop driving of the motor 81 and then reverse-rotate the motor 81 if the rate of change $\Delta I/\Delta t$ is not less than the predetermined value $\alpha$. The CPU 91 is also configured to, when it is detected after that that the current value I for driving the motor 81 is not more than a predetermined target current value Ita, continue to drive the motor 81.

An example of a logic circuit for drive-controlling the motor 81 will now be described with reference to FIG. 10.

The logic circuit includes, e.g., three AND circuits 111, 112, and 113.

The AND circuit 111 is configured to receive the value I of the current driving the motor 81 and the predetermined threshold value Ith inputted. The AND circuit 111 outputs Low (L) if the current value I is less than the threshold value Ith and outputs High (H) if the current value I is not less than the threshold value Ith. The AND circuit 111 is thus actually composed of a comparator or the like.

The AND circuit 112 is configured to receive the rate of change $\Delta I/\Delta t$ of the current value I and the predetermined value $\alpha$ inputted. The AND circuit 112 outputs Low (L) if the rate of change $\Delta I/\Delta t$ is less than the predetermined value a and outputs High (H) if the rate of change $\Delta I/\Delta t$ is not less than the predetermined value $\alpha$. The AND circuit 112 is thus also actually composed of a comparator or the like.

The AND circuit 113 ANDs an output from the AND circuit 111 and an output from the AND circuit 112. That is, the AND circuit 113 outputs High (H) only if the output from the AND circuit 111 is High (H), and the output from the AND circuit 112 is High (H) and outputs Low (L) at all other times.

The CPU 91 is configured to, on the basis of an output from the AND circuit 113, perform control of temporary stop and reverse rotation of the motor 81 if the output is High (H) and perform control to continue forward rotation of the motor 81 if the output is Low (L).

A drive controlling process for the motor 81 in the rotary self-advancing endoscope system 1 will be described with reference to FIG. 11.

When the process starts, the CPU 91 rotates the rotating cylindrical body 14 by forward-rotating the motor 81 (step S1). At the time, the CPU 91 acquires the RPM of the motor 81 from the rotation detecting portion 82 and performs control such that the motor 81 rotates at a constant speed at a predetermined RPM, i.e., the rotating cylindrical body 14 rotates at a constant speed.

The CPU 91 is detecting the value I of the current driving the motor 81 through the motor driving circuit 92 (step S2).

The CPU 91 determines whether the current value I is not less than the upper limit current value Imax (step S3).

If the current value I is less than the upper limit current value Imax, the CPU 91 also determines whether the rate of change $\Delta I/\Delta t$ of the current value I is not less than the predetermined value $\alpha$ (step S4).

If the rate of change $\Delta I/\Delta t$ of the current value I is not less than the predetermined value $\alpha$, the CPU 91 further determines whether the current value I is not less than the predetermined threshold value Ith (step S5).

If the rate of change $\Delta I/\Delta t$ of the current value I is less than the predetermined value $\alpha$ in step S4 or if the current value I is less than the predetermined threshold value Ith in step S5, a flow returns to step S1 described above to continue the forward rotation of the motor 81.

If it is determined in step S5 that the current value I is not less than the predetermined threshold value Ith (in the case, it has already been determined in step S4 that the rate of change $\Delta I/\Delta t$ is not less than the predetermined value $\alpha$), the CPU 91 calculates the target current value Ita (step S6).

The target current value Ita is calculated as a current value when the torque returns to a normal state. That is, a value obtained by adding some margin to a current value which would be reached at a time t2 if there had been no rapid increase in current value I since a time t1 in FIG. 9 is set as the target current value Ita.

Various methods can be used as a method for calculating the target current value Ita. As an example, the calculation can be performed in a following manner. First, the rate of change $\Delta I/\Delta t$ of the current value I before the time t1 (denoted by $\gamma$). Letting I(t1) be a current value at the time t1, a predicted current value Ifo at the time t2 when normal driving is performed is calculated as shown in Formula 1:

$$Ifo = I(t1) + \gamma(t2 - t1).$$

Accordingly, the target current value Ita can be calculated using a constant $\beta$ of not more than 1 for adding margin as follows:

$$Ita = Ith - (Ith - Ifo) \times \beta$$
$$= Ifo + (1 + \beta)(Ith - Ifo).$$

According to Formula 2, margin which is $(1-\beta)$ times a difference between the threshold value Ith and the predicted current value Ifo is set for the predicted current value Ifo. If $\beta$ is made to approach 1, the margin approaches 0, and the target current value Ita approaches the predicted current value Ifo.

The CPU 91 temporarily stops the driving of the motor 81 (step S7) and then reverse-rotates the motor 81 (step S8).

After the temporary stop and reverse rotation of the motor 81, the CPU 91 performs motor forward rotation for testing (test driving) (step S9) and detects the current value I (step S10), in order to determine whether the current value I has returned to a normal state.

The CPU 91 determines whether the detected current value I is not more than the target current value Ita (step S11). If the current value I is still larger than the target current value Ita, the flow returns to step S7 to temporarily stop and reverse-rotate the motor 81.

Note that the CPU 91 first performs the process in step S6 if it is determined YES in step S5, in order to exclude calculation of the target current value Ita from a loop from step S11 to step S7 (because it suffices to calculate the target current value Ita once). However, in practice, it is desirable to preferentially perform temporary stop of the motor 81 in step S7 and, if there is enough time left before later determination in step S11, perform the calculation in step S6 only once.

On the other hand, if it is detected in step S11 that the current value I is not more than the target current value Ita, the flow returns to step S1 to perform normal motor forward rotation.

After that, if it is determined in step S3 that the current value I has reached the upper limit current value Imax, the CPU 91 stops the motor 81 (step S12) and ends the process.

Figure 11:
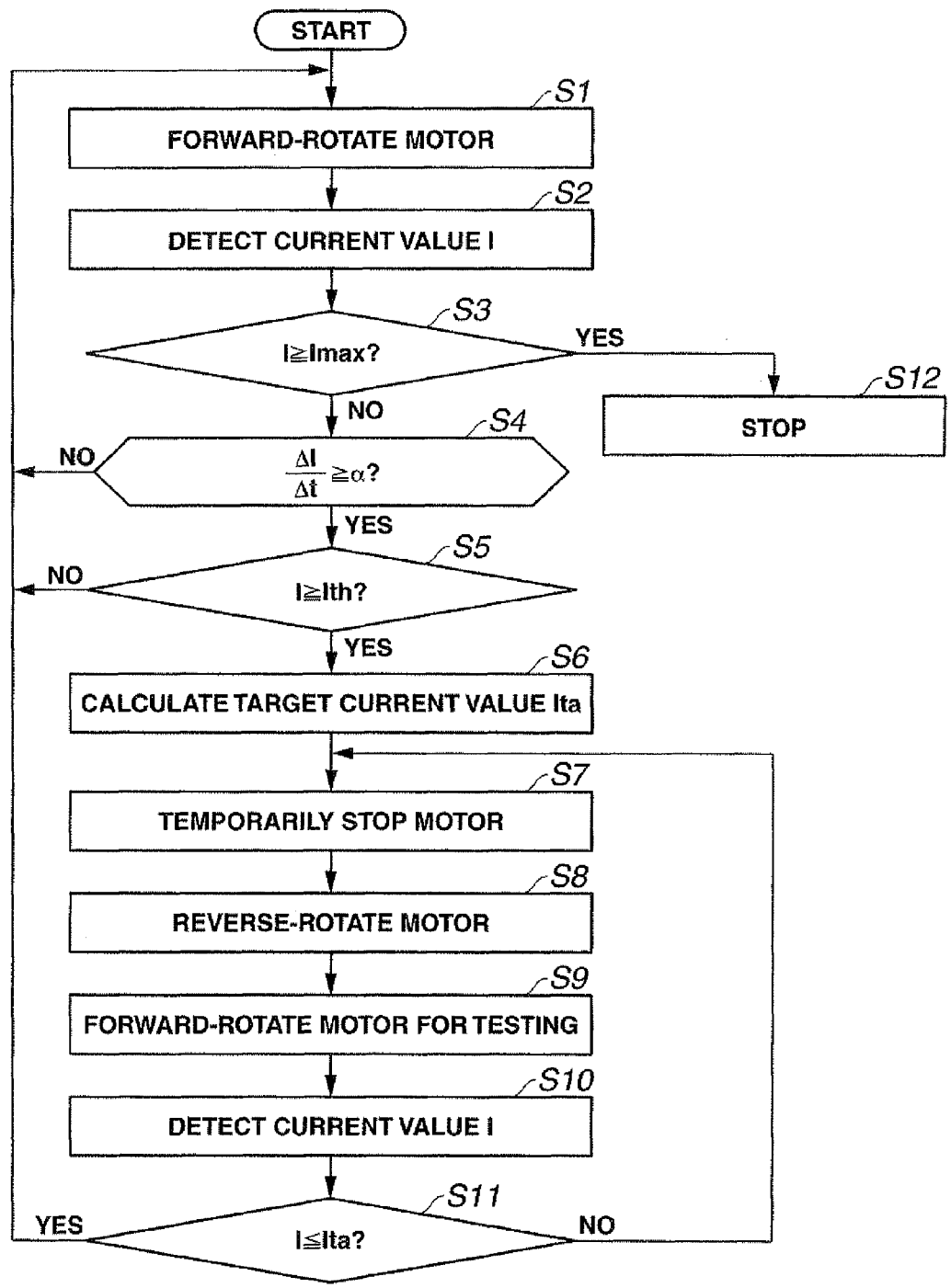
FIG. 11 is a flow chart showing drive control of the motor according to the embodiment.

A specific flow of the process as shown in FIG. 11 will be described with reference to FIG. 9.

As shown in FIG. 9, driving of the motor 81 is performed as normal until the time t1. Note that even if there is a small peak where the rate of change $\Delta I/\Delta t$ of the current value I exceeds the predetermined value $\alpha$ before the time t1, a process of temporarily stopping and reverse-rotating the motor 81 is not performed unless the current value I itself reaches the threshold value Ith. It is thus possible to avoid frequent temporary stop and reverse rotation of the motor 81.

Assume that the rate of change $\Delta I/\Delta t$ of the current value I exceeds the predetermined value $\alpha$ at the time t1. In the case, it is determined YES in step S4. Since the current value I is still less than the threshold value Ith at the time, it is determined NO in step S5, and the motor forward rotation in step S1 is continued.

After that, when the current value I reaches the threshold value Ith at the time t2, it is determined YES in step S5. Since two conditions, a condition that the current value I reaches the threshold value Ith and a condition that the rate of change $\Delta I/\Delta t$ of the current value I exceeds the predetermined value $\alpha$ are met, the driving of the motor 81 is temporarily stopped by the process in step S7 at the time t2.

The motor 81 is reverse-rotated for a predetermined time from a time t3 to a time t4 by the process in step S8.

The motor 81 is forward-rotated for testing for a predetermined short time from a time t5 to a time t6 by the process in step S9.

The current value I detected in the forward rotation for testing is above the target current value Ita in the example shown in FIG. 9. It is thus determined NO in step S11, and the driving of the motor 81 is temporarily stopped again at the time t6.

The process in step S8 is performed again, and the motor 81 is reverse-rotated for a predetermined time from a time t7 to a time t8.

After that, at a time t9, after the forward rotation for testing of the motor 81 in step S9, the current value I detected in step S10 is compared with the target current value Ita in step S11. In the example shown in FIG. 9, since the current value I is below the target current value Ita, the flow returns to step S1 to continue the forward rotation of the motor 81.

In the example shown in FIG. 9, after that, the current value I reaches the threshold value Ith. At the time, since the rate of change $\Delta I/\Delta t$ of the current value I is less than the predetermined value $\alpha$, the motor 81 is not temporarily stopped, and the forward rotation is continued.

At a time t10, when the current value I reaches the upper limit current value Imax, it is determined YES in step S3. In step S12, the forward rotation of the motor 81 is stopped, and the process ends.

Note that, in the above description, a process of reducing a load is performed when both of the first condition that the rate of change $\Delta I/\Delta t$ of the current value I becomes not less than the predetermined value $\alpha$ and the second condition that the current value I reaches the threshold value are met. The present invention, however, is not limited to this. A process of lessening torque may be performed when only one of the first and second conditions is met.

In the above description, stop and reverse rotation are performed to reduce a load. However, a certain degree of effect can be obtained only by stop.

According to the above-described embodiment, devising a drive pattern makes it possible to release elastic energy accumulated in the rotating cylindrical body 14 and restore the rotating cylindrical body 14 to a flexible state capable of efficiently transmitting a rotary force. This allows a reduction in load on the motor 81 and curbing heat generated by the motor 81. Use of the rotating cylindrical body 14 in the flexible state facilitates insertion into an examiners body. It is possible to allow the examinee's body side to return to a natural posture. Therefore, smooth and efficient insertion can be performed.

The above-described rotary self-advancing endoscope can be stably inserted without reducing propulsion.

According to the above-described embodiment, a stop of a drive source of a rotating cylindrical body caused by an increase in load is predicted, the drive source is temporarily stopped before the current value I reaches the upper limit current value Imax, and the drive source is driven again after a reduction in load. This configuration makes it possible to avoid a stop of the drive source. Accordingly, working efficiency of endoscopy can be improved.

At the time, since the drive source is not only temporarily stopped but also reverse-rotated, it is possible to efficiently reduce a load on the drive source in a shorter time.

Since a stop of the drive source is predicted on the basis of a rate of change with time of the current value I, it is possible to make a prediction while there is enough time before the current value I reaches the upper limit current value Imax.

It is determined at the time of predicting a stop of the drive source whether the current value I has reached the predetermined threshold value Ith. This makes it possible to avoid frequent temporary stop of driving due to influences of tiny noise and the like.

Since the threshold value Ith is calculated by multiplying the upper limit current value Imax by a predetermined coefficient of less than 1, it is possible to set the threshold value Ith to a value close to the upper limit current value Imax or set the threshold value Ith to a relatively low value with enough margin to the upper limit current value Imax, depending on the selected predetermined coefficient.

The drive source is driven for testing after temporary stop and reverse rotation of the drive source, and temporary stop of the drive source is repeated until the current value I becomes not more than the predetermined target current value Ita. Driving of the drive source is resumed only after it is determined that the current value I has become not more than the target current value Ita. This makes it possible to resume driving after it is ensured that a normal driving state has been restored.

Since calculation of the target current value Ita is performed using the predicted current value Ifo and threshold value Ith in the manner as shown in Formula 2, it is possible to restore the drive source to normal driving within an appropriate error range.

[Additional Remarks]

According to the embodiment of the present invention described above in detail, it is possible to implement following configurations.

[Additional Remark A1]

A rotary self-advancing endoscope system including:

a rotating cylindrical body which is provided at least a part on an outer periphery side of an insertion portion to be rotatable about an insertion axis of the insertion portion;

a drive source for rotating the rotating cylindrical body; and drive controlling means for controlling a rotation speed of the rotating cylindrical body to a non-constant rotation speed by controlling the drive source.

[Additional Remark A2]

The rotary self-advancing endoscope system according to Additional Remark A1, wherein the drive controlling means achieves the non-constant rotation speed by periodically switching between two or more different rotation speeds.

[Additional Remark A3]

The rotary self-advancing endoscope system according to Additional Remark A2, wherein the two or more different rotation speeds include a first constant rotation speed in one direction and a stop which is a rotation speed of 0.

[Additional Remark A4]

The rotary self-advancing endoscope system according to Additional Remark A3, wherein the two or more different rotation speeds further include a second constant rotation speed in another direction.

[Additional Remark A5]

The rotary self-advancing endoscope system according to Additional Remark A2, wherein the drive controlling means performs control such that periodicity of switching between the two or more different rotation speeds is changed depending on a time which has elapsed since a start of driving of the drive source.

[Additional Remark A6]

The rotary self-advancing endoscope system according to Additional Remark A2, wherein the drive controlling means performs control such that periodicity of switching between the two or more different rotation speeds is changed depending on an inserted length of the insertion portion into an examinee's body.

[Additional Remark A7]

The rotary self-advancing endoscope system according to Additional Remark A3, wherein the drive controlling means performs control to, immediately after a start of driving of the drive source, continuously drive the drive source in the one direction at the first constant rotation speed for a time longer than a time for subsequent periodical driving in the one direction at the first constant rotation speed.

[Additional Remark B1]

A method for driving a rotary self-advancing endoscope system including a rotating cylindrical body which is provided at least a part on an outer periphery side of an insertion portion, wherein the rotating cylindrical body is driven at a non-constant rotation speed.

[Additional Remark B2]

The method for driving the rotary self-advancing endoscope system according to Additional Remark B1, wherein the non-constant rotation speed is achieved by periodically switching between two or more different rotation speeds.

[Additional Remark B3]

The method for driving the rotary self-advancing endoscope system according to Additional Remark B2, wherein the two or more different rotation speeds include a first constant rotation speed in one direction and a stop which is a rotation speed of 0.

[Additional Remark B4]

The method for driving the rotary self-advancing endoscope system according to Additional Remark B3, wherein the two or more different rotation speeds further include a second constant rotation speed in another direction.

[Additional Remark B5]

The method for driving the rotary self-advancing endoscope system according to Additional Remark B2, wherein periodicity of switching between the two or more different rotation speeds is changed depending on a time which has elapsed since a start of driving of the drive source.

[Additional Remark B6]

The method for driving the rotary self-advancing endoscope system according to Additional Remark B2, wherein periodicity of switching between the two or more different rotation speeds is changed depending on an inserted length of the insertion portion into an examinee's body.

[Additional Remark B7]

The method for driving the rotary self-advancing endoscope system according to Additional Remark B3, wherein, immediately after a start of driving of the drive source, the drive source is continuously driven in the one direction at the first constant rotation speed for a time longer than a time for subsequent periodical driving in the one direction at the first constant rotation speed.

[Additional Remark B8]

The method for driving the rotary self-advancing endoscope system according to Additional Remark B1, wherein the rotating cylindrical body is manually driven at the non-constant rotation speed.

[Additional Remark C1]

A method for inserting an insertion portion into a body cavity by rotating a rotating cylindrical body having a helical projection at least a part on an outer periphery side, including:

a first step of moving the insertion portion forward in the body cavity by rotating one portion of the rotating cylindrical body about an insertion axis of the insertion portion, transmitting a rotary force of the one portion to another portion such that the other portion of the rotating cylindrical body rotates about the insertion axis, and rotating a whole of the rotating cylindrical body about the insertion axis; and a second step of rotating the one portion at a rotation speed lower than a rotation speed in the first step for releasing elastic energy accumulated in the rotating cylindrical body due to an inability to transmit the rotary force of the one portion to the other portion such that the other portion rotates about the insertion axis.

[Additional Remark C2]

The inserting method according to Additional Remark C1, wherein the rotation speed in the second step includes one or more stepwise decreasing rotation speeds which are lower than the rotation speed in the first step, and the first step and the second step are periodically and alternately executed.

[Additional Remark C3]

The inserting method according to Additional Remark C2, wherein the rotation speed in the second step includes a stop which is a rotation speed of 0.

[Additional Remark C4]

The inserting method according to Additional Remark C3, wherein the rotation speed in the second step includes a constant rotation speed in a rotation direction opposite to a rotation direction in the first step.

[Additional Remark C5]

The inserting method according to Additional Remark C2, wherein the first step and the second step are periodically and alternately executed with a cycle which changes depending on a time which has elapsed since a start of rotation of the rotating cylindrical body.

[Additional Remark C6]

The inserting method according to Additional Remark C2, wherein the first step and the second step are periodically and alternately executed with a cycle which changes depending on an inserted length of the insertion portion into the body cavity.

[Additional Remark C7]

The inserting method according to Additional Remark C2, further including a third step of, immediately after a start of rotation of the rotating cylindrical body, continuously rotating the one portion of the rotating cylindrical body in a same rotation direction as a rotation direction in the first step for a time longer than an execution time of the first step, which is subsequently and periodically alternated with the second step, in one cycle.

It will, of course, be appreciated that the present invention is not limited to the above-described embodiment and that various modifications and applications may be made without departing from the spirit and scope of the invention.

What is claimed is:

1. A rotary self-advancing endoscope system for accessing a body cavity comprising:
    an endoscope having an insertion portion for visualizing an interior of the body cavity;
    a rotating cylindrical body having a lumen configured to receive the insertion portion and being configured to rotate about an insertion axis of the insertion portion;
    a helical projection disposed on an outer surface of the rotating cylindrical body, wherein, in response to a rotation of the rotating cylindrical body, the helical projection induces a relative movement along the insertion axis between the cylindrical body and the body cavity;
    a drive source for rotating the rotating cylindrical body; and
    drive controlling means for controlling the drive source using a plurality of modes including a first mode of driving the drive source at a first RPM and a second mode of driving the drive source at a second RPM different from the first RPM,
    wherein the drive controlling means causes a rotation speed of the rotating cylindrical body to be a non-constant rotation speed which changes periodically at fixed intervals by performing automatic control to periodically switch the drive source between the plurality of modes at fixed intervals.

2. The rotary self-advancing endoscope system according to claim 1, wherein
    the drive source rotates one portion of the rotating cylindrical body about the insertion axis of the insertion portion, transmits a rotary force of the one portion to another portion such that the other portion of the rotating cylindrical body rotates about the insertion axis, and rotates a whole of the rotating cylindrical body about the insertion axis, and
    the drive controlling means automatically controls the drive source to, in the first mode, rotate the one portion of the rotating cylindrical body in a forward rotation direction for causing the insertion portion to self-advance in a body cavity and to, in the second mode, rotate the one portion at a rotation speed lower than a rotation speed for the first mode for releasing elastic energy accumulated in the rotating cylindrical body due to an inability to transmit the rotary force of the one portion to the other portion such that the other portion of the rotating cylindrical body rotates about the insertion axis.

3. The rotary self-advancing endoscope system according to claim 1 wherein the endoscope comprises an operable bending portion disposed on a distal portion of the insertion portion, and the operable bending portion is provided on a distal side of the rotating cylindrical body.

4. The rotary self-advancing endoscope system according to claim 3 wherein the distal side of the rotating cylindrical body is under no constraints during the rotation and configured to be rotationally free.

5. A rotary self-advancing endoscope system comprising:
    a rotating cylindrical body which is located on at least a part on an outer periphery side of an insertion portion to be rotatable about an insertion axis of the insertion portion;
    a drive source for rotating the rotating cylindrical body;
    drive controlling means for controlling the drive source using a plurality of modes including a first mode of driving the drive source at a first RPM and a second mode of driving the drive source at a second RPM different from the first RPM;
    rotation detecting means for detecting an RPM of the rotating cylindrical body by detecting a driving state of the drive source; and
    current detecting means for detecting a value of a current supplied to the drive source, wherein
    the drive controlling means calculates a rate of change with time by calculating a variance in the value of the current between the value of the current at a first time and the value of the current at a predetermined time after the first time and dividing the variance by the predetermined time, while drive-controlling the drive source such that the RPM detected by the rotation detecting means remains constant in the first mode and, if the calculated rate of change is not less than a predetermined value, performs automatic control to temporarily stop the drive source for a predetermined time in the second mode.

6. The rotary self-advancing endoscope system according to claim 5, wherein the drive controlling means performs automatic control to temporarily stop the drive source for the predetermined time if the rate of change is not less than the predetermined value, and the value of the current being detected by the current detecting means is not less than a predetermined threshold value.

7. The rotary self-advancing endoscope system according to claim 6, wherein
    the drive controlling means further performs automatic control to stop the drive source if the value of the current being detected by the current detecting means is not less than a predetermined upper limit current value, and
    the predetermined threshold value is calculated by multiplying the upper limit current value by a predetermined number of less than 1.

8. The rotary self-advancing endoscope system according to claim 5, wherein
    the drive source is capable of forward driving and reverse driving, and
    the drive controlling means performs automatic control to temporarily stop the drive source for the predetermined time and temporarily reverse-drive the drive source.

9. The rotary self-advancing endoscope system according to claim 6, wherein the drive controlling means performs automatic control to drive the drive source for testing after temporarily stop the drive source for the predetermined time, repeat temporary stopping of the drive source until the value of the current detected by the current detecting means during test driving becomes not more than a predetermined target current value, and resume driving of the drive source when the value has become not more than the target current value.

10. The rotary self-advancing endoscope system according to claim 9, wherein,
    letting Ith be the threshold value, and Ita be the target current value,
    the drive controlling means calculates a predicted current value Ifo which would be obtained at a time when temporary stop of the drive source is started if the drive source were normally driven and calculates the target current value Ita using a predetermined constant $\beta$ of not more than 1 by a following formula:

$$Ita = Ith - (Ith - Ifo) \times \beta.$$

11. The rotary self-advancing endoscope system according to claim 5 wherein the endoscope comprises an operable bending portion disposed on a distal portion of the insertion portion, and the operable bending portion is provided on a distal side of the rotating cylindrical body.

12. The rotary self-advancing endoscope system according to claim 11 wherein the distal side of the rotating cylindrical body is under no constraints during the rotation and configured to be rotationally free.

* * * * *